(12) United States Patent
Mintchev

(10) Patent No.: US 7,343,201 B2
(45) Date of Patent: Mar. 11, 2008

(54) GASTROINTESTINAL MOTILITY CONTROL

(75) Inventor: Martin P. Mintchev, Calgary (CA)

(73) Assignee: University Technologies International Inc., Calgary (CA)

( * ) Notice: Subject to any disclaimer, the term of this patent is extended or adjusted under 35 U.S.C. 154(b) by 493 days.

(21) Appl. No.: 11/000,325

(22) Filed: Nov. 29, 2004

(65) Prior Publication Data

US 2005/0137643 A1 Jun. 23, 2005

Related U.S. Application Data

(60) Provisional application No. 60/525,138, filed on Nov. 28, 2003.

(51) Int. Cl.
*A61N 1/36* (2006.01)

(52) U.S. Cl. ...................................... 607/40

(58) Field of Classification Search ............... 607/40, 607/41, 45, 61, 72, 73, 133
See application file for complete search history.

(56) References Cited

U.S. PATENT DOCUMENTS

| 4,612,934 | A | * | 9/1986 | Borkan ..................... 607/62 |
| 5,690,691 | A | | 11/1997 | Chen et al. |
| 5,836,994 | A | | 11/1998 | Bourgeois |
| 5,861,014 | A | | 1/1999 | Familoni |
| 5,995,872 | A | | 11/1999 | Bourgeois |
| 6,026,326 | A | | 2/2000 | Bardy |
| 6,083,249 | A | * | 7/2000 | Familoni ..................... 607/40 |
| 6,091,992 | A | | 7/2000 | Bourgeois et al. |
| 6,115,635 | A | | 9/2000 | Bourgeois |
| 6,205,359 | B1 | * | 3/2001 | Boveja ..................... 607/45 |
| 6,216,039 | B1 | | 4/2001 | Bourgeois |
| 6,238,423 | B1 | | 5/2001 | Bardy |
| 6,243,607 | B1 | | 6/2001 | Mintchev et al. |
| 6,327,503 | B1 | | 12/2001 | Familoni |
| 6,449,511 | B1 | | 9/2002 | Mintchev et al. |
| 6,535,764 | B2 | | 3/2003 | Imran et al. |
| 6,542,776 | B1 | | 4/2003 | Gordon et al. |
| 6,571,127 | B1 | | 5/2003 | Ben-Haim et al. |

(Continued)

OTHER PUBLICATIONS

Isabelle Le Blanc-Louvry et al "Gastric Stimulation: Influence of Electrical Parameters on Gastric Emptying in Control and Diabetic Rats" Research Article; p. 1-13 from MBC Surgery, vol. 2; Downloaded from www.biomedcentral.com/1471-2482/2/5; Jul. 2002.

(Continued)

*Primary Examiner*—Kennedy J. Schaetzle
(74) *Attorney, Agent, or Firm*—Christensen O'Connor Johnson Kindness PLLC

(57) ABSTRACT

A method and a multichannel implantable device are described for partial or complete restoration of impaired gastrointestinal motility, or for disturbing and/or partially or completely blocking normal gastrointestinal motility using one or multiple microsystem-controlled channels of circumferentially arranged sets of two or more electrodes which provide externally-invoked synchronized electrical signals to the smooth muscles via the neural pathways.

20 Claims, 15 Drawing Sheets

U.S. PATENT DOCUMENTS

| | | |
|---|---|---|
| 6,591,137 B1 | 7/2003 | Fischell et al. |
| 6,600,953 B2 | 7/2003 | Flesler et al. |
| 6,606,523 B1 | 8/2003 | Jenkins |
| 6,615,084 B1 | 9/2003 | Cigaina |
| 6,684,104 B2 * | 1/2004 | Gordon et al. ............... 607/40 |
| 6,826,428 B1 | 11/2004 | Chen et al. |
| 6,907,293 B2 * | 6/2005 | Grill et al. .................. 607/39 |
| 6,993,391 B2 | 1/2006 | Flesler |
| 2002/0072780 A1 * | 6/2002 | Foley ........................ 607/40 |
| 2006/0047323 A1 | 3/2006 | Foley |

OTHER PUBLICATIONS

J. Chris Eagon and Keith A. Kelly "Effect of Gastric Pacing on Canine Gastric Motility and Emptying"; 1993; The American Physiological Society; p. G767-G774.

Mauro Bortolotti "The "Electrical Way" to Cure Gastoparesis" AJG, vol. 97 No. 8, 2002; p. 1874-1883.

J. Chris Eagon and N.J. Soper; Abstract of "Gastrointestinal Pacing"; Surg Clin North Am; Dec. 1993; 73(6): 1 page.

* cited by examiner

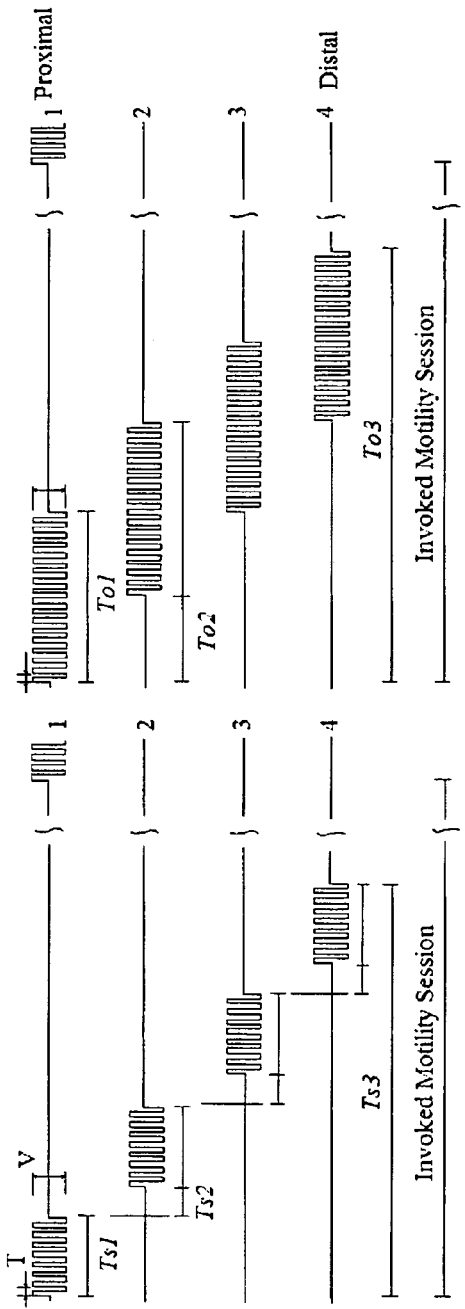
FIG. 2A
FIG. 2B
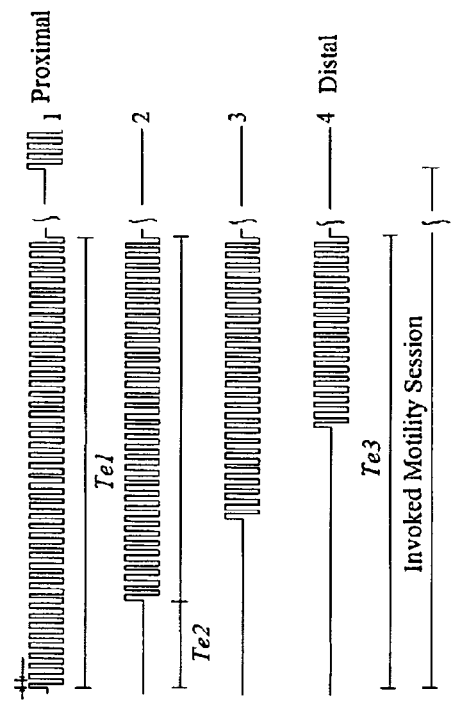
FIG. 2C

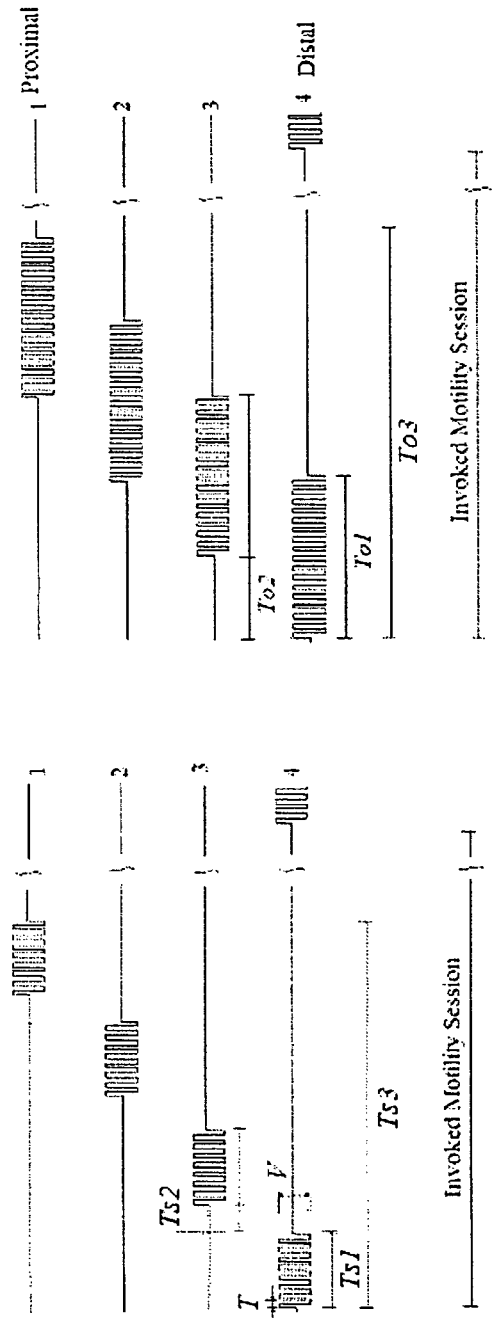
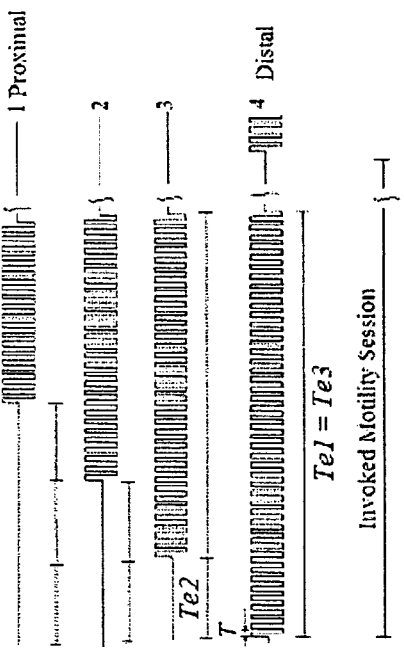
FIG. 5A
FIG. 5B
FIG. 5C

GASTROINTESTINAL MOTILITY CONTROL

CROSS-REFERENCE TO RELATED APPLICATIONS

This application claims the benefit of priority under 35 U.S.C. 119(e) of U.S. provisional application No. 60/525,138 filed Nov. 28, 2003.

BACKGROUND OF THE INVENTION

Gastrointestinal motility control is of interest to medical practitioners, including to treat disorders of the gastrointestinal tract and to treat conditions related to the function of the gastrointestinal tract such as obesity. Previous patents have described various stimulation techniques for entraining or stimulating gastrointestinal motility, but these methods enhance or manipulate the spontaneously existing gastrointestinal electrical activity, thus hoping to indirectly affect gastrointestinal motility, since spontaneously existing motility can be regarded as a result of the existing electrical slow waves. In our previous patents and in the published research that followed, we suggested a third method for stimulation using sequentially administered trains of high frequency (50-500 Hz) voltages.

SUMMARY OF THE INVENTION

In the present application we provide according to an aspect of the invention a method and apparatus for overriding the spontaneously existing gastrointestinal (GI) motility and producing artificial peristalsis completely asynchronously with the spontaneously existing mechanical phenomena in the GI tract, in a given GI organ, or in a portion thereof, using trains of external voltages with wide range of frequencies (5-50,000 Hz), wide range of duty cycles (10-100%) and wide range of amplitudes (3-30 V peak-to-peak). In a further aspect of the invention, we provide a method and apparatus for producing preliminary externally controlled contractions in the sphincter region or regions of the said GI organ or in a portion of it (for example, the pylorus in the stomach). The adjacent acetylcholine (ACh) patches in the vicinity of the said sphincter region are exhausted due to the prolonged invoked contractions, so that the sphincter inevitably relaxes as a result. In a still further aspect of the invention, we provide a method and apparatus that invokes externally controlled GI peristalsis after this sphincter relaxation is achieved, so that content is propelled through the said sphincter. And in a further aspect of the invention, we describe an implantable microsystem device which can achieve the described functionalities, which is either autonomously or transcutaneously powered. In addition, there is provided a way to disturb spontaneously existing peristalsis, or to completely or partially override it so that the process of spontaneous GI motility is asynchronously adversely affected as an avenue to treat morbid obesity, which can make use of the same device.

Further description of the invention is contained in the detailed disclosure and claims that follow.

BRIEF DESCRIPTION OF THE FIGURES

There will now be described preferred embodiments of the invention, with reference to the drawings, by way of illustration only and not with the intention of limiting the scope of the invention, in which like numerals denote like elements and in which:

FIGS. 2A-2C show a configuration of synchronized patches of external signals: sequential (A), overlapping (B) and embedded (C);

FIGS. 5A-5C show exemplary external signal patterns for producing reversed peristalsis;

DETAILED DESCRIPTION OF PREFERRED EMBODIMENTS

Figure 1A:
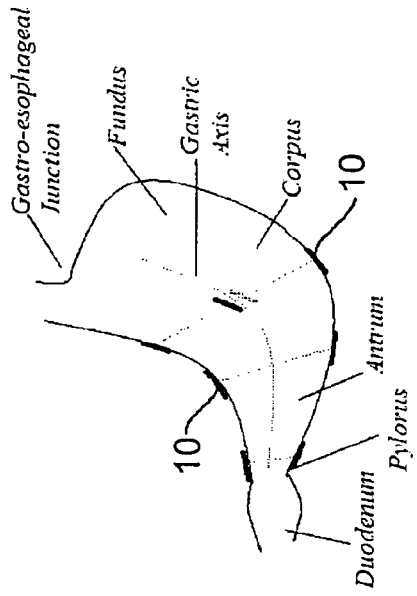
FIGS. 1A-1D show placing of electrodes on portions of the gastrointestinal tract according to the invention.
Figure 1C:
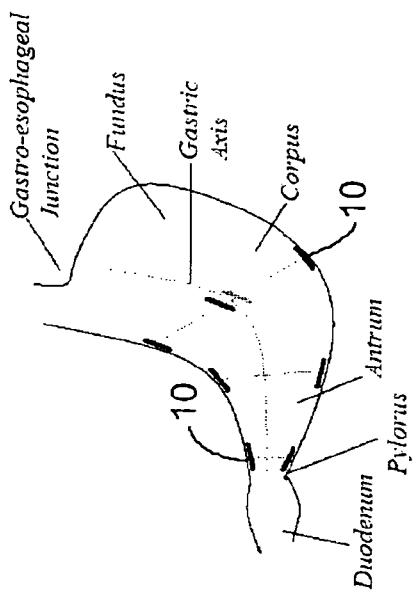
Figure 1B:
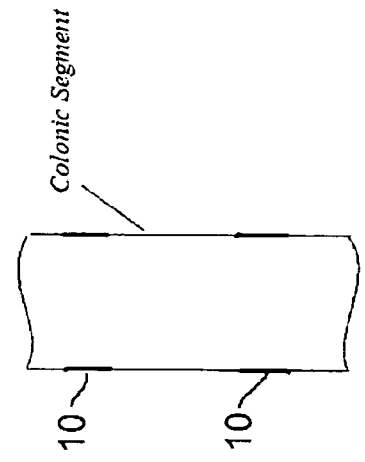
Figure 1D:
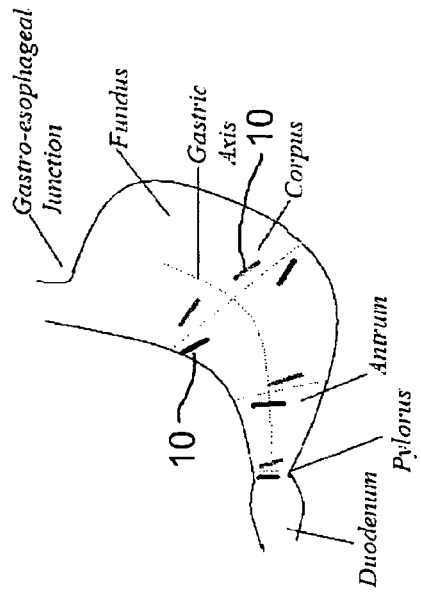
Figure 3A:
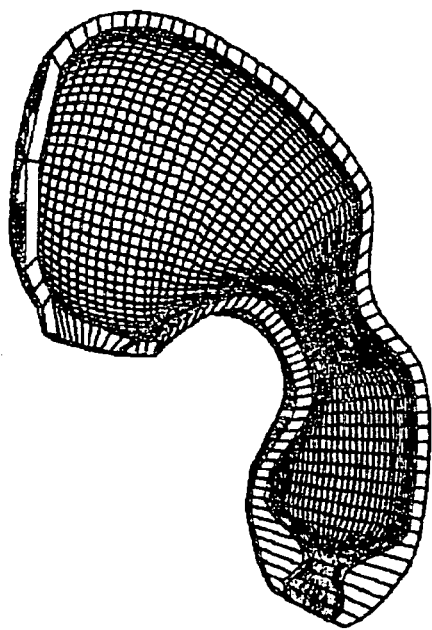
FIGS. 3A-3D and 4A-4D are three dimensional views showing respectively the effect of the sequential and embedded excitation patterns on the stomach.
Figure 3B:
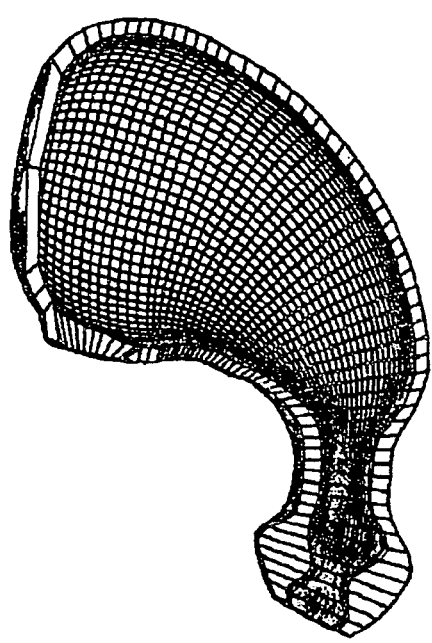
Figure 3C:
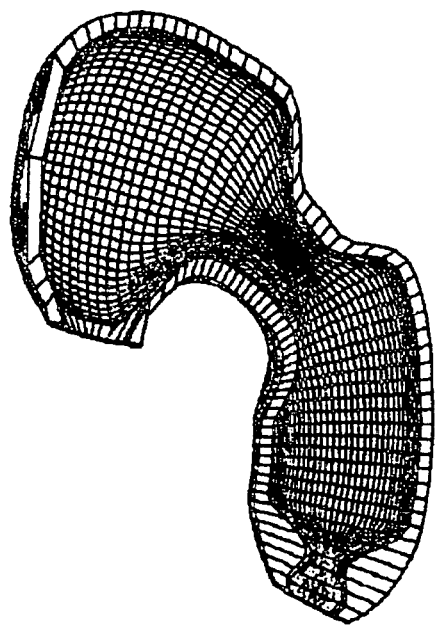
Figure 3D:
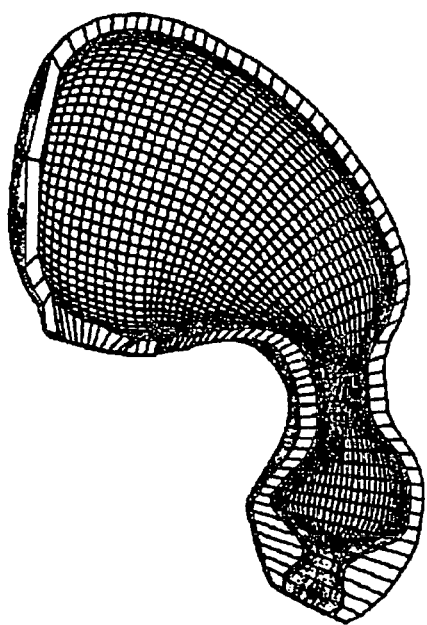
Figure 4A:
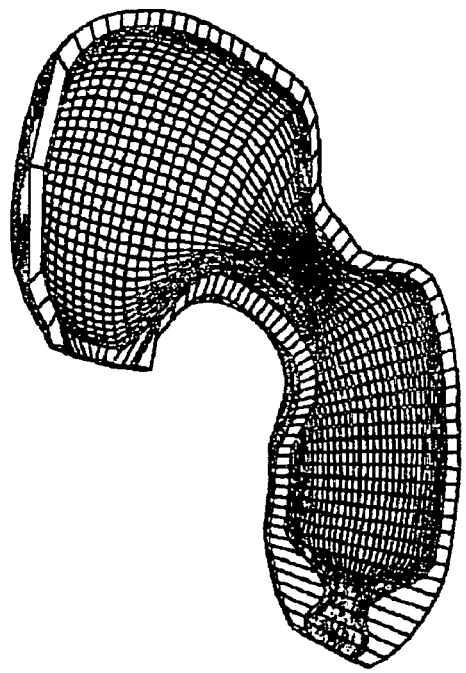
Figure 4B:
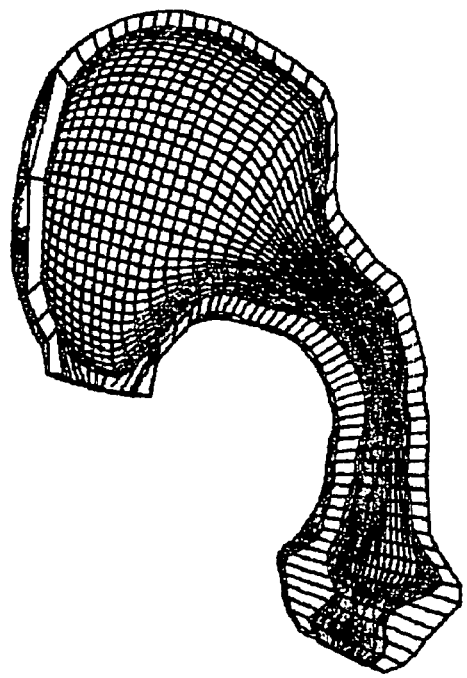
Figure 4C:
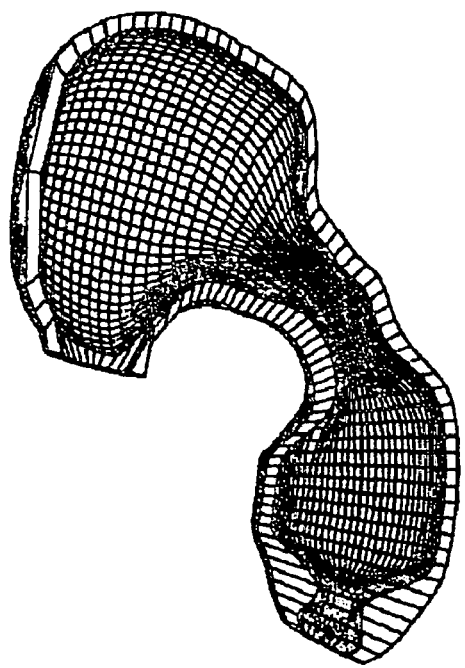
Figure 4D:
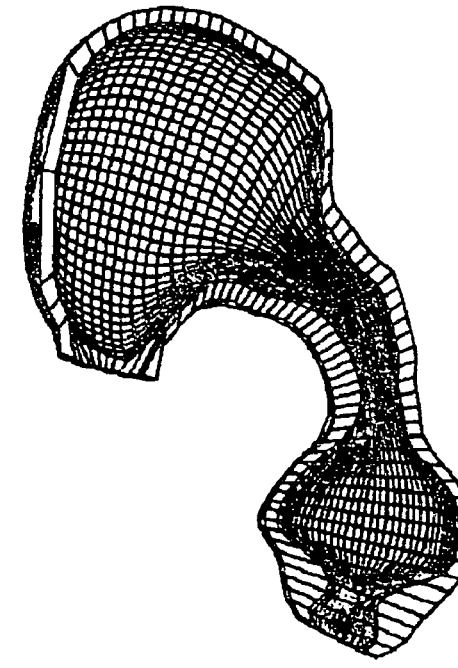
Figure 6A:
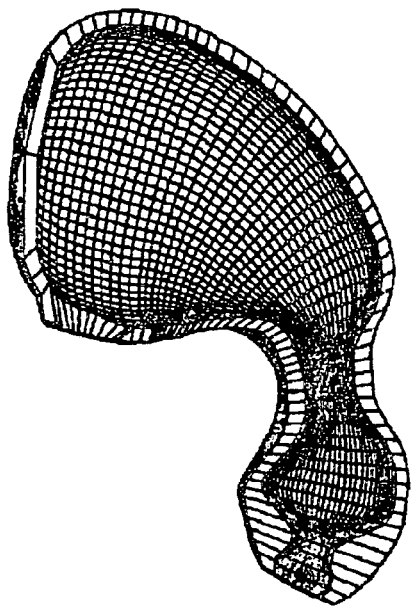
FIGS. 6A-6D are three dimensional views showing effect of a sequential pattern of excitatory signals on the stomach.
Figure 6B:
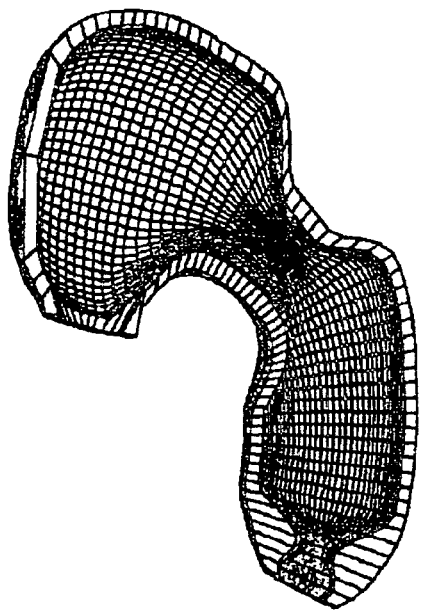
Figure 6C:
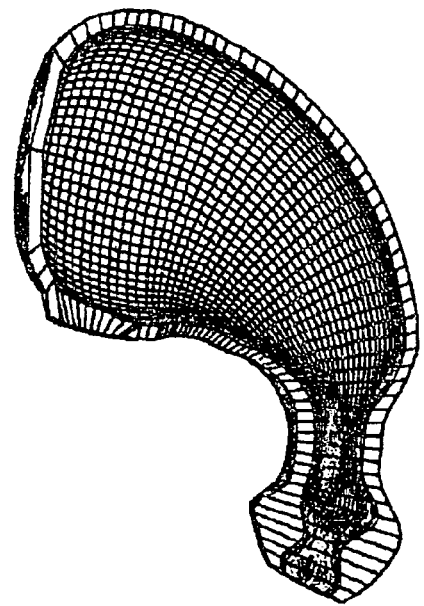
Figure 6D:
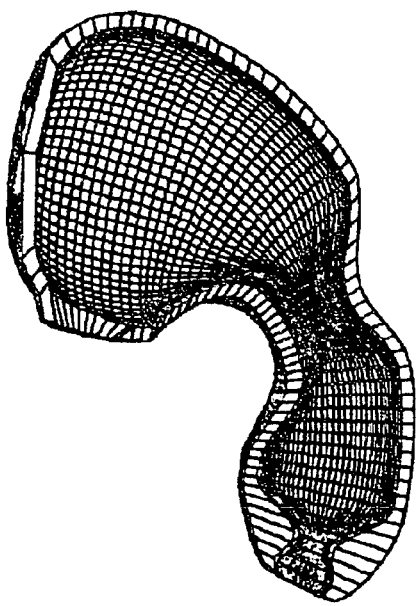

In this patent document, "comprising" means "including" and does not exclude other elements being present. In addition, a reference to an element by the indefinite article "a" does not exclude the possibility that more than one of the elements is present. A reference to an element is not restricted to the particular form of the element disclosed, but includes functional equivalents now known or hereafter developed.

Electrodes for obtaining control of gastrointestinal tract motility are implanted either from the serosal or the mucosal side of the particular gastrointestinal organ (e.g. the stomach, the colon, the esophagus, etc.), and their axes could be either collinear or perpendicular to the organ axis. The electrodes are implanted in pairs. Each electrode pair consists of two electrodes, one being a ground (reference) and the other the active electrode. One or several electrode pairs (depending on the circumference of the organ in the area where the electrodes are implanted) form a local electrode set, which is implanted corresponding to an imaginary line perpendicular to the organ axis. One or several local electrode sets can be implanted along the axis of the gastrointestinal organ, either from the mucosal or from the serosal side.

FIGS. 1A-1D show sample electrode configurations for the stomach (A, B and C) and for a segment of the colon (D). Electrodes 10 can be collinear with the organ axis (A, B, D), or perpendicular to it (C). The length of the electrodes is between 0.2 and 5 cm. The distance between electrode sets can be between 1.5 and 10 cm. Electrodes from a given pair and from adjacent sets should not touch, and the minimal distance between them should be 1 cm. The electrodes can be implanted subserosally (A, D, C) or from the mucosal side (B). Electrodes implanted on the posterior wall of the organ are lighter in color. The electrodes of a given set are arranged correspondingly to imaginary lines perpendicular to the organ axis (shown in lighter color as well).

External signals are supplied to the electrodes 10 to achieve gastrointestinal motility control. The external signals supplied to the electrode sets, although synchronized between themselves, are completely asynchronous with the spontaneously existing motility in the particular GI organ, and override it, rather than stimulating or enhancing it in any way. The frequency of the synchronized signals ranges from 5 to 50,000 Hz, and their amplitudes range from 3 V peak-to-peak to 30 V peak-to-peak. The duty cycle can vary from 10 to 100%, for example 50% to 90%. The synchronized signals are delivered in patches with three basic configurations, sequential, overlapping, and embedded, and the pause between the patches or bursts ranges from 3 seconds to 3 minutes in a single session (FIGS. 2A-2C). Multiple sessions can be administered. The current delivery capability of the microsystem can be estimated considering the average total current consumption per unit muscular thickness of GI tissue per electrode pair, which is approximated as 3 mA/mm. With the assumption that the thickness of the muscle is in the range of 2.5 mm to 3.5 mm, the average total current drawn by the tissue will be in the range of 7.5 mA to 10.5 mA.

FIGS. 2A-2C show a configuration of the synchronized patches of external signals: sequential (A), overlapping (B) and embedded (C). Each invoked motility session can last from 3 seconds to 3 minutes. The time $T_3$ represents the composite duration of the external signals from all channels. This time, combined with an appropriate relaxation time (post-motility pause), constitute the overall invoked motility session time. The relaxation time is at least 2 times longer that the composite duration of the external signals in all channels, so that a complete relaxation of the smooth muscles can be achieved. The pause between successive patches in the sequential pattern (A) can be from 0 seconds to the duration of the patch itself, Ts1. The time between the end of Ts1 in the proximal channel and the start of the signal patch in the next more distal channel is Ts2. The shift time To2 in the overlapping pattern can be in the range between To1 and To1−T, where T is the period of the high-frequency pulses (T=1/f, f=5 to 50,000 Hz) and To1 is the duration of the external signal in channel 1. The delay time Te2 in the embedded pattern can be from Te1−T to Te1/2, where Te1 is the duration of the external signal in channel 1 (which in this pattern coincides with the overall duration of the motility control session). The amplitude V of the stimuli can be in the range of 3-30 V (peak-to-peak). The sequential pattern of FIG. 2A is illustrated in FIGS. 3A-3D, and the embedded pattern of FIG. 2C is illustrated in FIGS. 4A-4D, using a three-dimensional model of the stomach. Extensive tests have been performed on 8 acute dogs and the anticipated contractile response resulting from the production of invoked peristalsis was verified both visually and with force transducers implanted in the vicinity of the implanted electrode sets.

Invoked peristalsis using synchronized local contractions can be produced also in the opposite direction, a concept that could be labeled invoked reversed peristalsis. This opportunity could be very important for the treatment of morbid obesity, since reversed peristalsis can delay gastric emptying and affect in a controlled way the desire of a given patient to consume food. Similarly to the invoked distal peristalsis, three different patterns of the external synchronized patches can be employed. FIGS. 5A-5C represent various external signal patterns for producing reversed peristalsis. Since the microsystem producing the patterns is programmable, comfort levels specific to a given patient can be determined in order to produce the desired controlled peristalsis without inducing nausea and vomiting which are usual side effects of abnormal gastric motor function. FIGS. 5A-5C show sequential (A), overlapping (B) and embedded (C) synchronized patches of external signals aiming at producing reversed peristalsis. Each invoked motility session can last from 3 seconds to 3 minutes and the strength of the contractions is completely controllable by the microsystem, so that appropriate voltage treshholds can be selected in order to avoid invoked nausea and vomiting in the patient. The time $T_3$ represents the composite duration of the external signals from all channels. This time, combined with an appropriate relaxation time (post-motility pause), constitute the overall invoked motility session time aiming at producing reversed peristalsis. The relaxation time is at least 2 times longer that the composite duration of the external signals in all channels, so that a complete relaxation of the smooth muscles can be achieved. The pause between successive patches in the sequential pattern (A) can be from 0 seconds to the duration of the patch itself, Ts1. The time between the end of Ts1 in the distal channel and the start of the signal patch in the next more proximal channel is Ts2. The shift time To2 in the overlapping pattern can be in the range between To1 and To1−T, where T is the period of the high-frequency pulses (T=1/f, f=5 to 50,000 Hz) and To1 is the duration of the external signal in the most distal channel 4. The delay time Te2 in the embedded pattern can be from Te1−T to Te1/2, where Te1 is the duration of the external signal in the most distal channel 4 (which in this pattern coincides with the overall duration of the motility control session). The amplitude V of the stimuli can be in the range of 3-30 V (peak-to-peak). The sequential patterns from FIG. 5A are illustrated in FIGS. 6A-6D. It should also be mentioned that inducing controlled reversed peristalsis in the antrum affects the mechanoreceptors, which are abundant in the area, if appropriate voltage levels for the external signals are utilized. Thus, rather than inducing nausea and vomiting, a perception of early satiety could result. This, by itself, could be a substantial avenue for treating morbid obesity.

Figure 7:
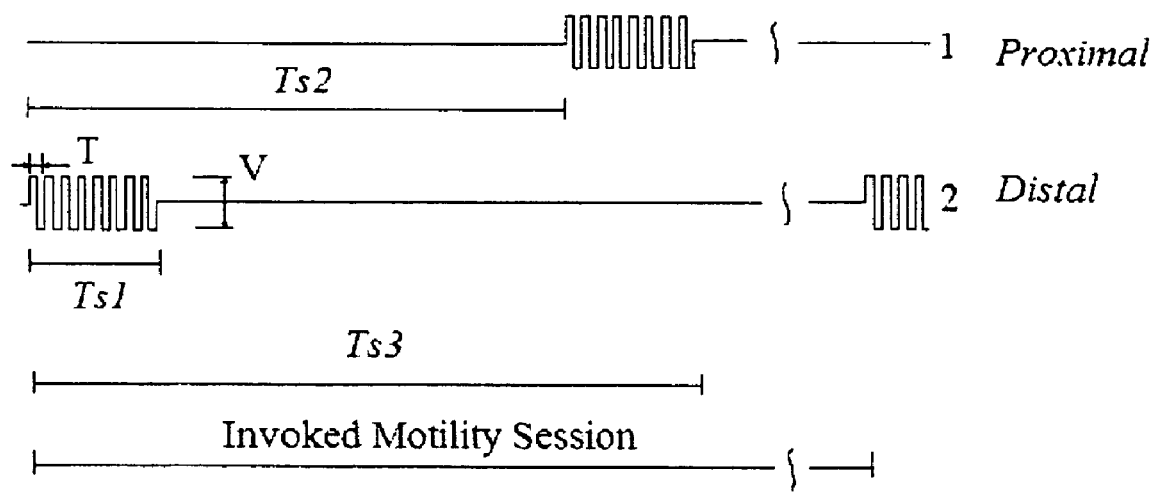
FIG. 7 illustrates a single session of a sample pattern to invoke asynchronous contractile desynchronization.
Figure 8B:
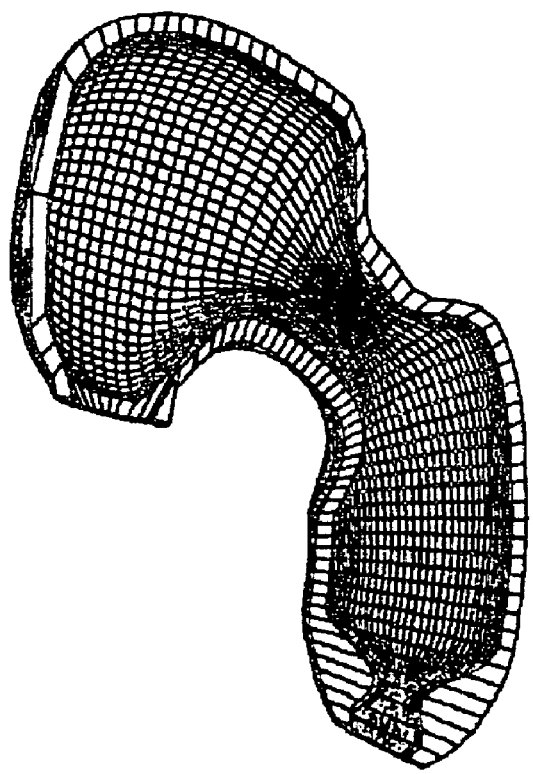
FIGS. 8A-8B depict contractions resulting from the excitation pattern of FIG. 7 in a three-dimensional mathematical model of the stomach.
Figure 8A:
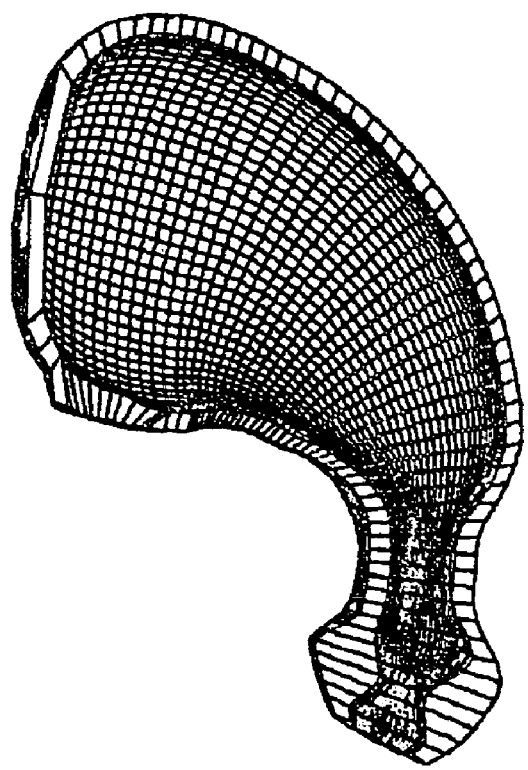

Rather than producing reversed peristalsis, gastric content can be retained in the stomach simply by invoking controlled asynchronous contractile desynchronization. Similarly to the invoked peristalsis patterns described above, this technique also overrides the spontaneously existing contractile pattern in the stomach, but imposing a pattern which aims not to move content distally (normal forward persitalsis), nor to move it in a proximal direction (reversed peristalsis) in a synchronized fashion, but to keep the content in prolonged contact with the antral mechanoreceptors simply by "shaking it" back and forth, thus inducing in the patient a perception of early satiety. This can be achieved by the repetitive asynchronous administration of the external voltage signals controlling minimized number of implanted electrode sets (two sets could be sufficient, one proximal and one distal). FIG. 7 illustrates single session of a sample pattern to invoke asynchronous contractile desynchronization, and FIGS. 8A-8B depict the resulting contractions in a three-dimensional mathematical model of the stomach, which was verified experimentally in acute tests. The session can be repeated in random sequence to prolong the "shaking" effect.

Figure 9A:
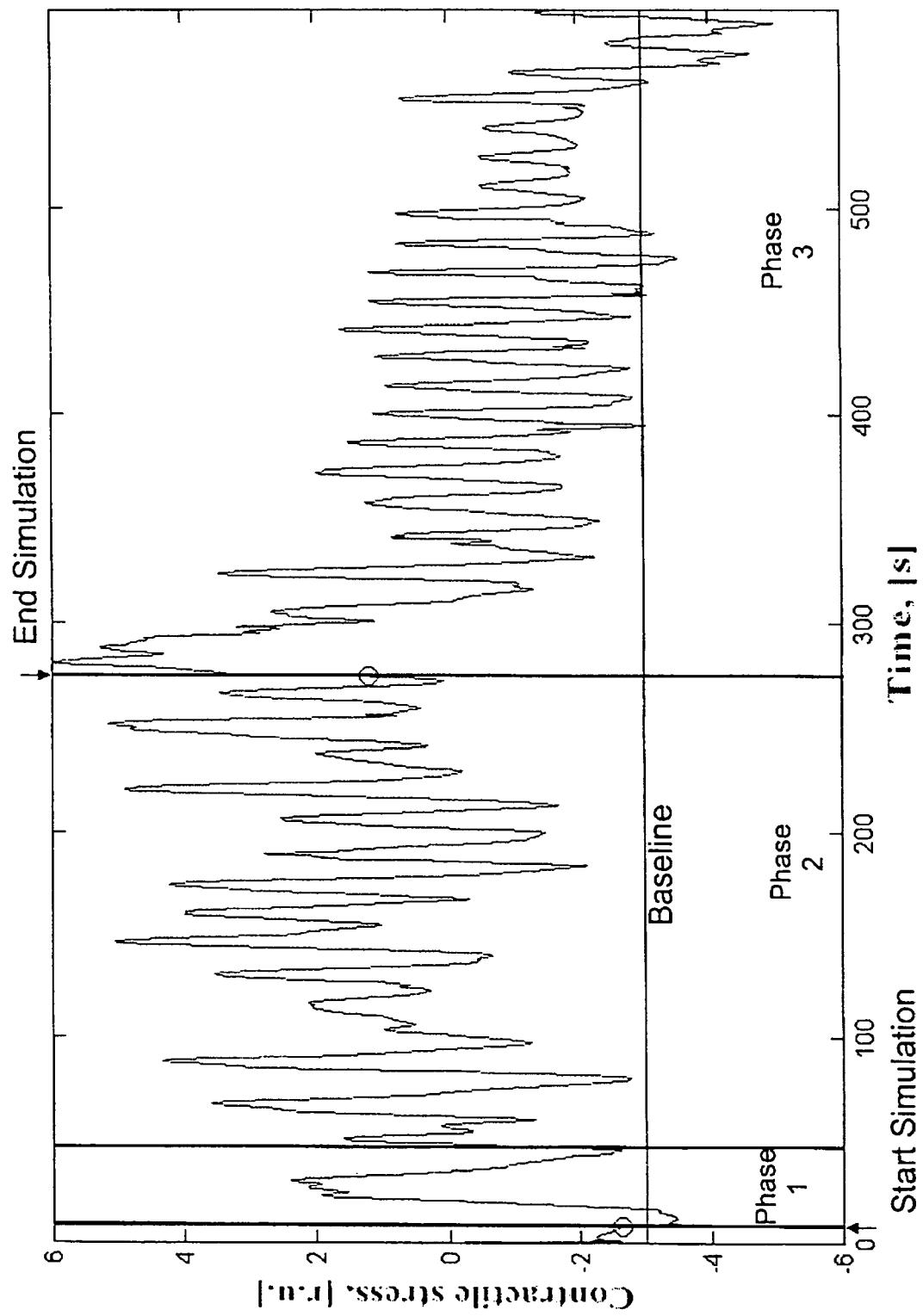
FIG. 9A shows the cyclic nature of the smooth muscle response to external neural electrical control assessed with implanted force transducers in the vicinity of the electrodes.
Figure 9B:
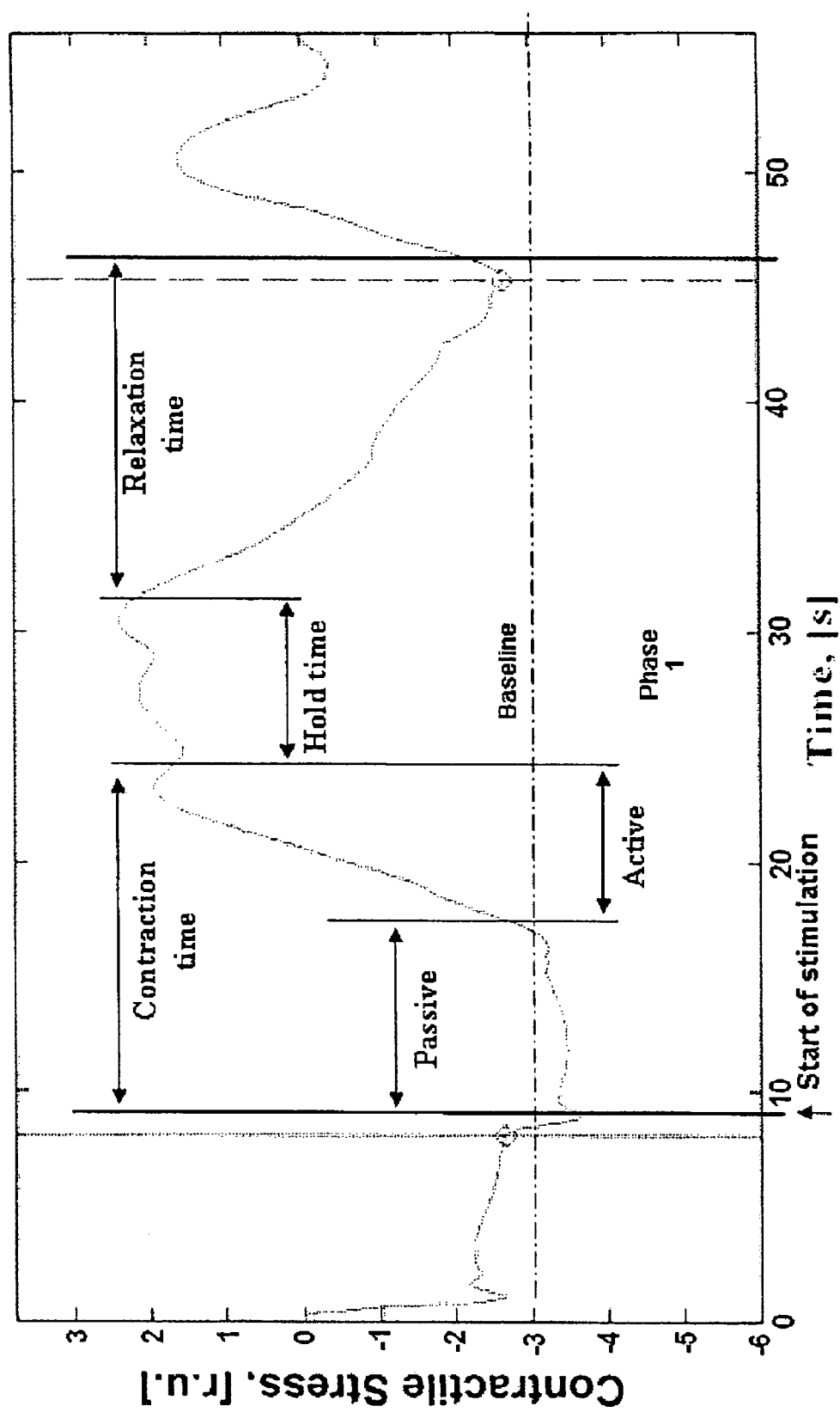
FIG. 9B is a detail of a cycle from FIG. 9A.

For sphincter control, a pair of electrodes is implanted on or in the vicinity of the sphincters of the organ (for example, on the pylorus of the stomach) so that the sphincters can be controlled (brought into a contracted stage to prevent content passing, or forced into relaxation to permit content passing) by utilizing or exhausting the available acetylcholine (ACh) patches in the vicinity of the said sphincters. These patches are released as a result of prolonged exposure to high frequency pulse trains, and the timing of this release, as well as the time it takes to exhaust these patches are known to us from extensive experimental work (FIGS. 9A, 9B). FIG. 9A shows the cyclic nature of the smooth muscle response to external neural electrical control assessed with implanted force transducers in the vicinity of the electrodes. Prolonged motility control session clearly reveals the cycles of sustained contractions followed by relaxations, although the continuous external electrical control was maintained (FIG. 9A). Within about 25-30 seconds the ACh patches in the vicinity of the muscle (e.g. the pylorus) get exhausted and the muscle relaxes even though the external electrical control continues. These timings are illustrated in details in FIG. 9B, which can be regarded as a zoomed-in averaged cycle extracted from FIG. 9A.

Figure 10A:
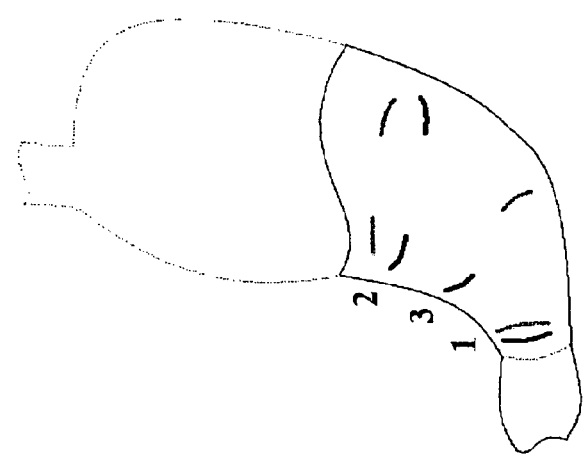
FIGS. 10A and 10B show electrode configurations for invoked peristalsis of a stomach.
Figure 11A:
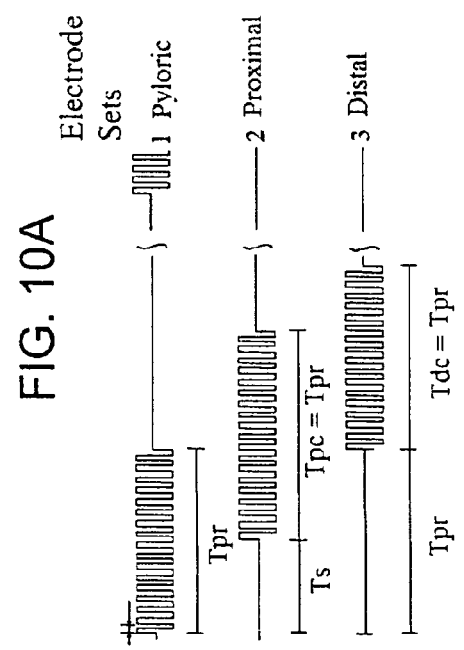
FIGS. 11A and 11B show excitation patterns for excitation of the corresponding electrode sets 1, 2, 3 in FIGS. 10A and 10B respectively.
Figure 10B:
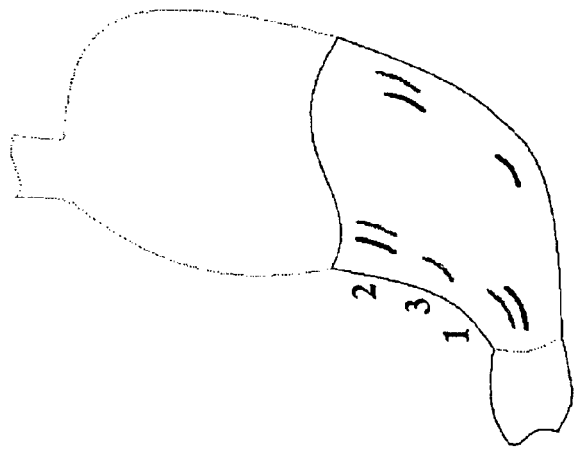
Figure 11B:
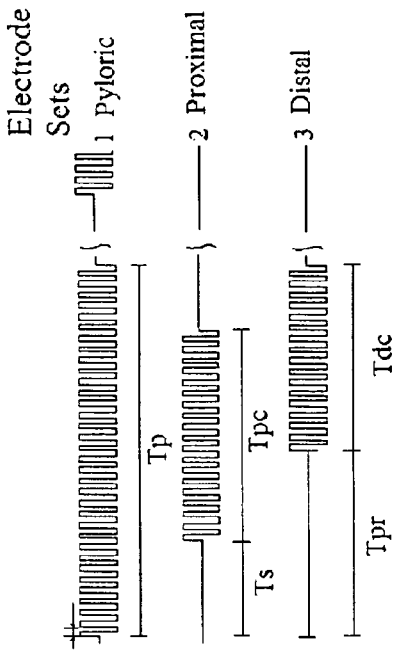

Specifically, the timings for achieving forced pyloric relaxation have been measured in large dogs by implanting force transducer in the vicinity of the pylorus, and utilizing pyloric electrode configurations depicted in FIGS. 10A-10B with the excitation scheme shown in FIGS. 11A and 11B respectively. If, for example, a relaxation of the pylorus is required to propel content, continuous externally invoked and controlled contraction of this sphincter takes place until the ACh patches in its vicinity are exhausted, and the pylorus relaxes while the ACh patches recover. During this period of induced relaxation, the content is propelled using a synchronously produced invoked peristalsis under microprocessor control. Since the relaxation of the pylorus is also invoked under microprocessor control, the invoked peristalsis and the pyloric relaxation can be completely synchronized for maximally efficient gastric emptying.

Alternatively, knowing for how long the pylorus can be kept contracted, and how often its cyclic contractions can be invoked, gastric emptying could be significantly slowed down in particular time intervals during or after food intake. In addition, pyloric control during fasting periods can be utilized to manipulate the feelings of hunger or satiety by interrupting the spontaneously-existing migrating myoelectrical complex in the stomach, again under microprocessor control and without synchronizing this activity with the spontaneously existing motility but by overriding it asynchronously.

FIGS. 11A and 11B show an example of synchronizing preliminary pyloric contraction for the purpose of exhausting the ACh patches in the vicinity of the pylorus using electrode set 1 with the contractions produced using two other electrode sets (proximal, 2 and distal, 3). The region of the stomach subject to invoked peristalsis is shown darker. Electrode configurations can be perpendicular to the gastric axis (FIG. 10A), or collinear with it (FIG. 10B). The electrode set 1, implanted in the pyloric region, delivers external voltage trains for the time Tpr needed to exhaust the ACh patches in the vicinity of the pylorus (about 25-30 seconds), resulting in pyloric relaxation at the very end of this time period. About half way through Tpr (e.g. around the $10^{th}$-$15^{th}$ second), the delivery of external voltage pulses to the proximal electrode set starts, and after Tpr, the delivery of external voltage pulses to the distal electrode set takes place (FIG. 11A). Alternatively, the delivery of external voltage trains can continue with the pyloric electrode set 1 for the entire session, since the pylorus will relax after Tpr in a cyclic fashion anyway (FIG. 11B). The latter technique provides a prolonged, albeit cyclic, pyloric relaxation, but inevitably is related to higher power consumption.

Figure 12:
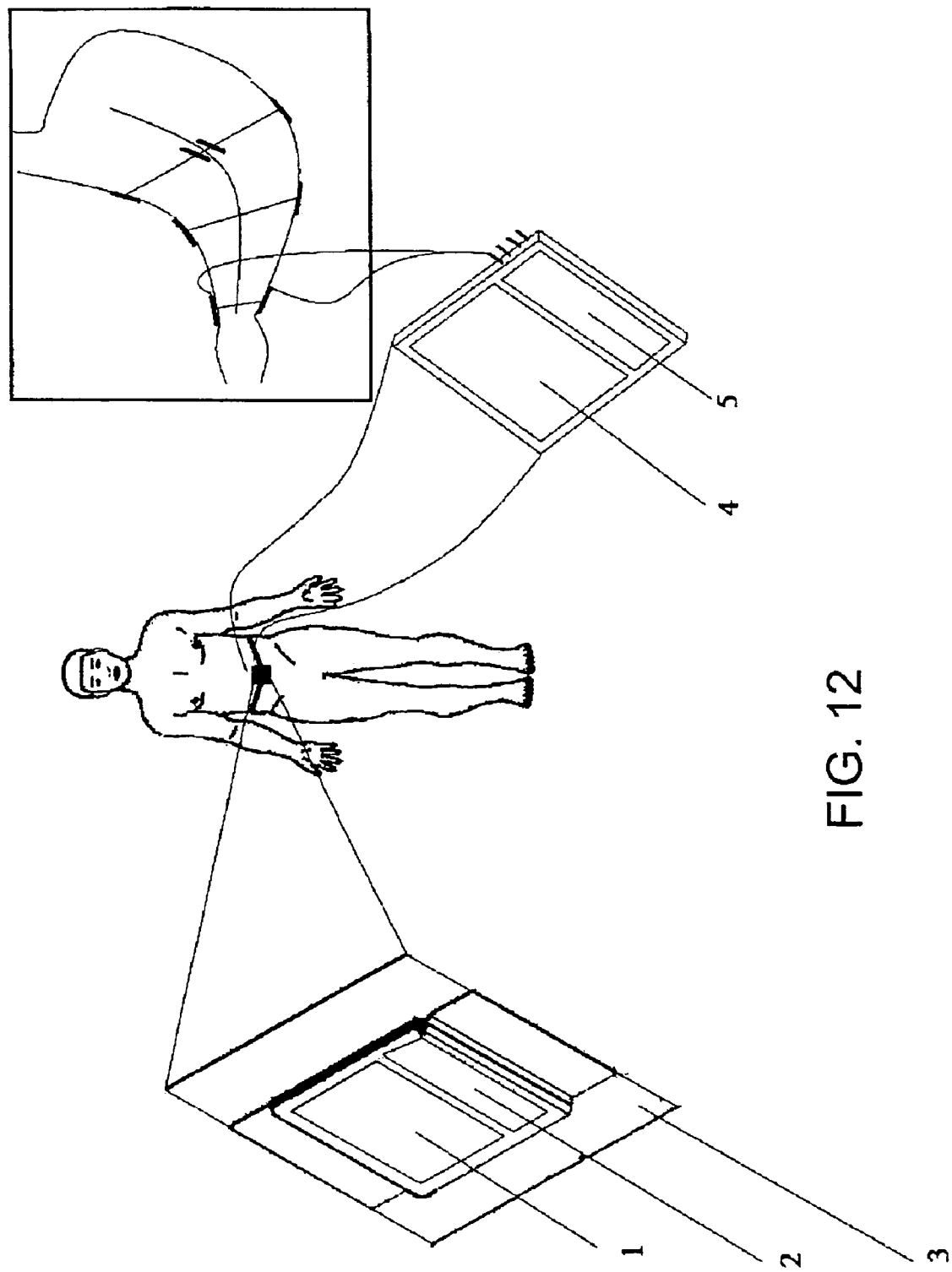
FIG. 12 is a perspective view, with an inset showing an internal detail, of apparatus for carrying out the invention.
Figure 13:
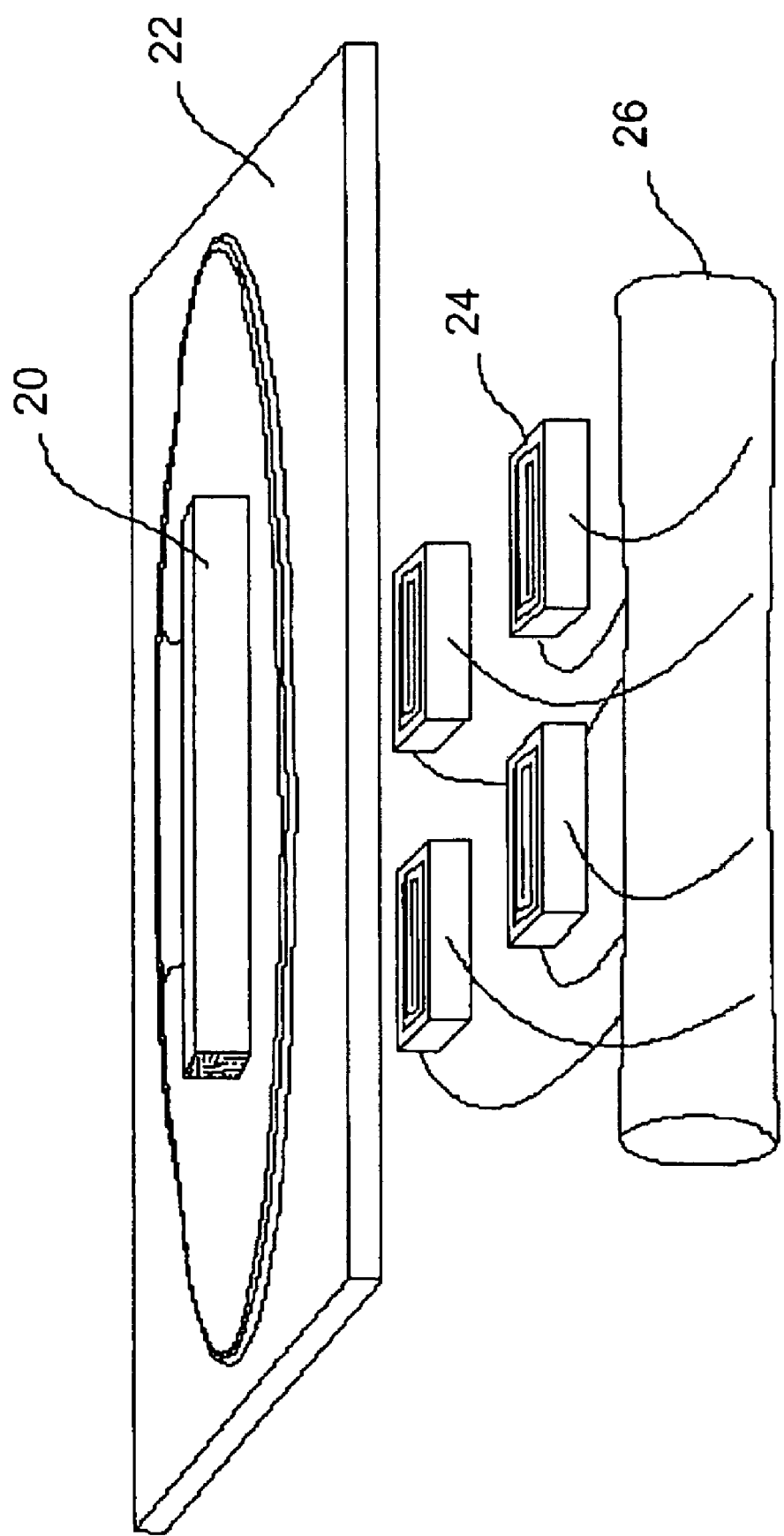
FIG. 13 shows schematically an arrangement for delivering excitation pulses without transcutaneous wires.

Apparatus for carrying out the invention is shown in FIGS. 12, 13, 14A and 14B. The power supply of the proposed implantable microsystem can be achieved either by (a) autonomous battery; (b) autonomous battery which is rechargeable through a transcutaneous inductive link facilitated by an abdominal belt periodically worn by the patient (preferably during sleep) (FIG. 12); or (c) transcutaneous power transfer facilitated by an abdominal belt worn by the patient during the periods of the desired gastrointestinal organ control (FIG. 13).

FIG. 12 shows a distributed microsystem setup. The external control is administered via abdominal belt (left), in which the transmitting inductive coil for transcutaneous power transfer is positioned (1), along with the associated microcontroller-based electronics (2, see also FIGS. 13 and 14B). The belt is attached to the body in the abdominal area (3). The implanted microsystem (right) is sutured on the inner side of the abdominal wall right under the abdominal bell center. It contains receiving coil (4) which is aligned with the transmitting coil and microcontroller-based electronics (5, see also FIG. 14A). In case of autonomous non-rechargeable battery-based power supply for the implanted microsystem, transmitting and receiving coils are not necessary and the dimensions of both microsystems could be reduced. The implanted microsystem is shown with four channels, and the pyloric channel is connected to the schematic replica of the stomach of FIG. 1B.

FIG. 13 depicts an external transmitter 20 located over the skin 22 in the abdominal belt worn by the patient can be utilized to power one or multiple implants 24 in various sections of the gut 26 (e.g. in the colon). The transcutaneous power supply link is inductor-based.

Figure 14A:
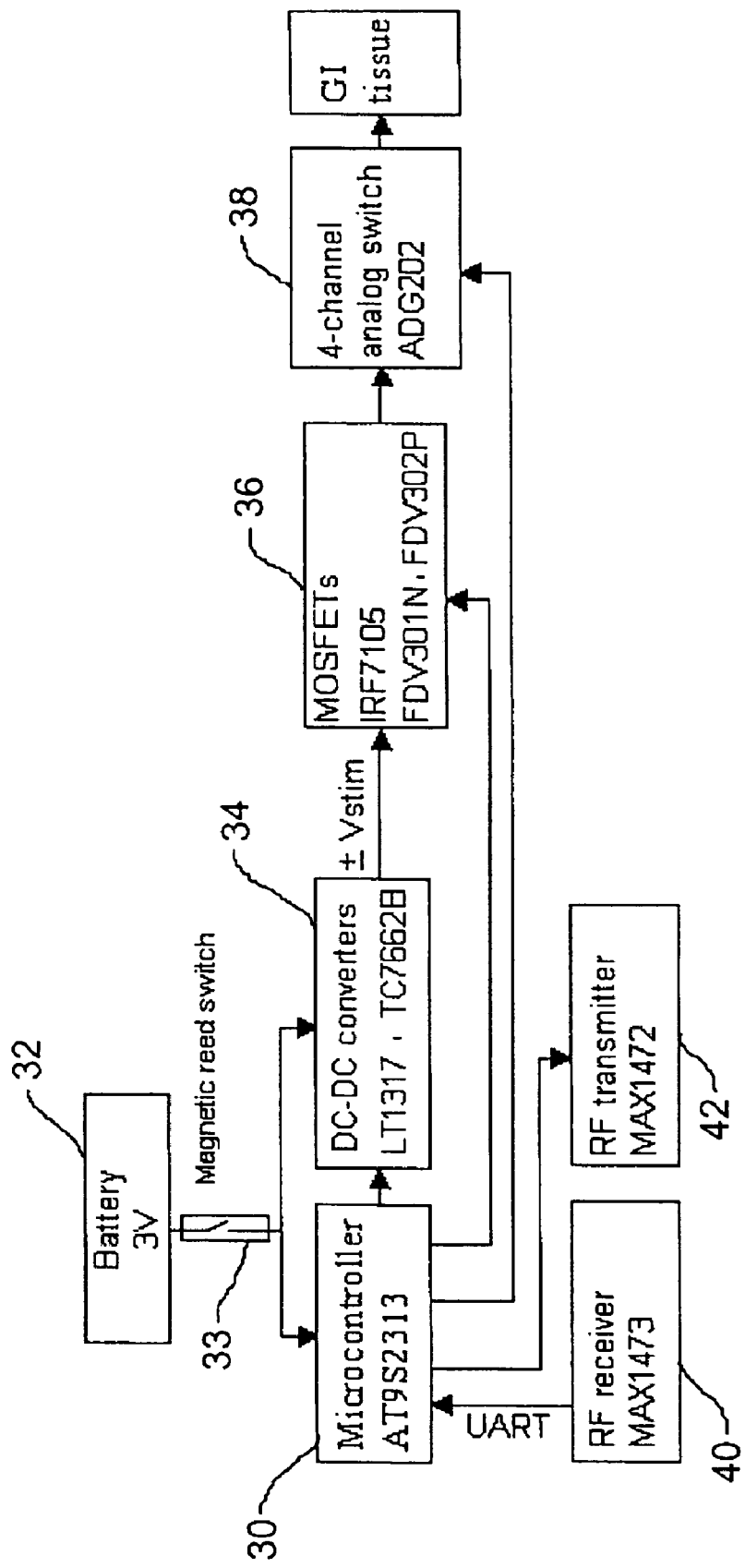
FIGS. 14A and 14B are block diagrams of apparatus for carrying out the invention.
Figure 14B:
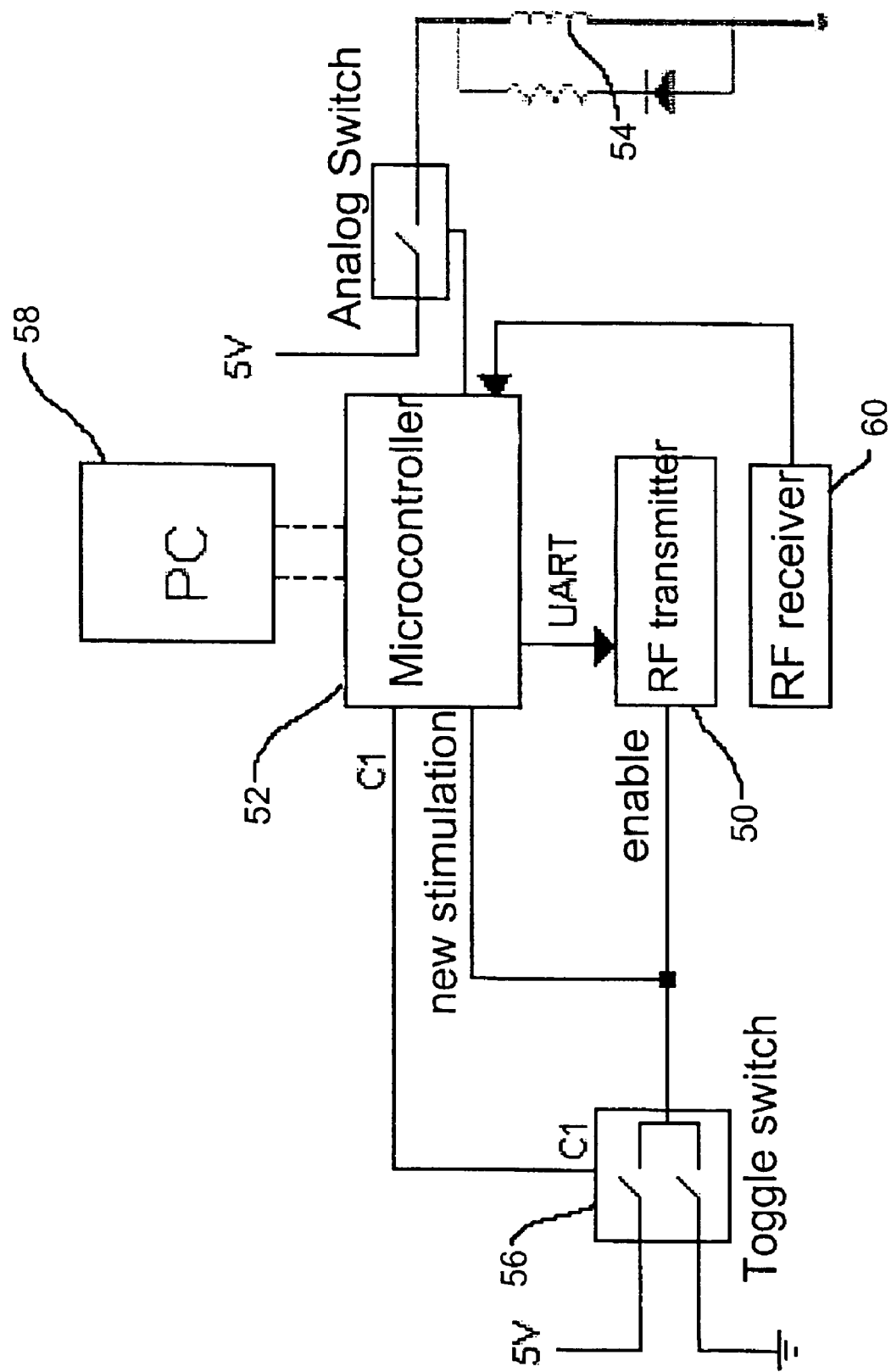

The overall block diagrams of the entire system are presented in FIGS. 14A and 14B. Both the implantable device and the external controlling device are microsystems, each including a microcontroller. FIGS. 14A and 14B show block diagrams of the implantable device (FIG. 14A) and the controlling device located in the abdominal belt in a discrete electronic implementation. Very-Large-Scale-Integration (VLSI) of the same concept is also possible and could be preferred if further device miniaturization is desired. In this particular implementation the battery 32 of the implantable device can be autonomous or externally rechargeable. The communication between the controlling microsystem of FIG. 14B and the implant of FIG. 14A is provided with radio-frequency tranceivers.

The system includes an external control circuitry and an implantable device. Once the implant is in place, the external control circuitry can be utilized to control the motility control parameters, the number of motility control sessions and the pause between successive sessions. The implantable microsystem of FIG. 14A includes five major blocks: (1) microcontroller 30; (2) DC-DC converters 34; (3) MOSFETs 36; (4) analog electronic switch 38; and (5) wireless transmitter 40 and receiver 42 (see FIG. 14A). The microcontroller 30 may be for example model AT90S2313 (Atmel, San Jose, Calif.) programmed to generate the digital motility control pulses and to control the output of the DC-DC conversion stage. In addition, it determines the duration of each motility control session and the overlap between successive channels via the analog switch 38. The motility control parameters (amplitude, frequency, overlap, and session length) can vary from one motility control session to another. The microcontroller 30 is pre-programmed with a set of different values for each motility control parameter. In addition, a default value is specified for each parameter. The operator can choose the desired value of each parameter from this pre-determined list using a transcutaneous control link. The clock frequency for the microcontroller 30 has been chosen to be 20 KHz. This low crystal frequency was chosen to minimize the switching power losses in the microcontroller 30. The maximum frequency will be 500 Hz, resulting in a minimum pulse width of 2 ms. A 20 KHz crystal has an instruction cycle of 50 μs, which is sufficiently large for generating 2 ms or slower pulses.

The RF receiver 40, for example a MAX1473 (Maxim, Dallas, Tex.), is used to receive serial wireless data containing the choice of the motility control parameters from the external portable control unit of FIG. 14B. This data is transmitted serially and in an asynchronous mode to the microcontroller 30 using the UART input. The data transfer rate (baud rate) is set to 125 bit/s for operation with a crystal frequency of 20 KHz. The microcontroller 30 will sample the data at 16 times the baud rate. If the UART input does not detect a start bit for data transfer in the first 5 seconds after power-up, the microcontroller 30 will start a motility control session using its default parameters. The microcontroller 30 will send a 'confirmation byte' at the onset of the control pattern (5 s after startup) to the external control circuit via the RF transmitter. A byte with all one bits represents the onset of motility control with new parameters, while a byte with all zeros represents the onset of motility control with default parameters. The DC-DC conversion block 34 includes two integrated circuits (ICs): LT1317 (Linear Technology, Milpitas, Calif.), a step-up voltage converter, and TC7662B (Microchip, Chandler, Ariz.), a charge-pump voltage inverter. These two ICs convert the supplied 3V to the desired amplitude ($V_{stim}$). $V_{stim}$ is in the range of ±5V to ±10V and can be adjusted by the microcontroller 30. The MOSFET stage 36 utilizes for example two logic transistors FDV303N and FDV304P (Fairchild, South Portland, Me.) and two power transistors, which are included in one package IRF7105 (International Rectifier, El Segundo, Calif.). The logic FETs 36 have a low gate threshold voltage and can be switched by the 3V logic square wave produced by the microcontroller 30. These logic transistors drive the gates of the power FETs, which convert the digital square wave to a bipolar analog output of the same frequency and an amplitude equal to $V_{stim}$. The output of the transistors 36 is directed to the stimulating electrodes 10 through a four-channel analog switch 38 (for example ADG202, Analog Devices, Norwood, Mass.). Each of the four switch channels closes upon receiving an enable command from the microcontroller 30. The analog switch 38 also isolates each electrode 10 from the successive electrode sets. The microcontroller 30 preferably receives both the necessary electrical power and the required stimulation pattern information transcutaneously through the receiver 40, optionally also using an inductive coil as part of the receiver 40. The microcontroller 30 then converts the obtained stimulation pattern information into real stimulation sequences delivered to the implanted electrodes by controlling operation of the logic FETs 36. On conclusion of the sending of a stimulation sequence, the microcontroller 30 then reports back to an external controller the success or failure of the delivered stimulation sequences. Success or failure may be determined for example by sensors that detect whether a specified contraction has taken place and send a corresponding signal to the microcontroller 30.

A portable microcontroller-based controller circuit allows the user to select the appropriate parameters for producing artificially invoked peristalsis (frequency, amplitude, overlap between channels and session length). This battery-operated control circuit is external to the body, and is worn by the patient in an abdominal belt. A digital wireless transmitter 50 (MAX1472, Maxim, Dallas, Tex.) is used to transmit the chosen motility control parameters to the implanted motility control device (FIG. 14A). The external controller 52 can also be used to adjust the number of the successive motility control sessions (1-4) as well as the pause period between the successive sessions (30-120 s). The external circuit turns the implanted motility control device on or off for adjustable lengths of time by controlling a normally open magnetic reed switch 33 that is integrated in the implanted system. The reed switch 33 is placed in series with the implanted battery 32. The controller 52 turns the magnetic reed switch 33 on by energizing a coil 54 to generate a static magnetic field. FIG. 14B shows the design of the external controller.

The external controller has a toggle switch 56 that allows the user to implement either a default motility control session (using the implanted motility control device's default parameters) or a new motility control session. The parameters for the new motility control session are downloaded to the external unit's microcontroller 52 from a PC 58 via an RS232 link. These parameters are transferred from the microcontroller 52 to the wireless transmitter 50 using the UART line, at a baud rate equal to the implanted circuit's baud rate of 125 bit/s. The wireless transmitter 50 then sends this information to the implanted circuit (FIG. 14A). In the case of motility control session with default parameters, the RF transmitter 50 will be disabled and the microcontroller 52 will not send any data to it. The microcontroller 52 will simply turn the implanted circuit on via the reed switch 33. The implanted circuit of FIG. 14A will interpret lack of incoming information from the transcutaneous link as a sign that default motility control session must be performed. The RF receiver 60 is used for receiving the 'confirmation byte' from the implanted stimulator. The microcontroller 52 will send a signal to de-energize the coil t+5 seconds after startup, where t represents the time length of each motility control session.

The methods and apparatus disclosed here radically differ from previously proposed gastrointestinal stimulation techniques, at least since:

(a) it does not stimulate or enhance the spontaneously existing gastrointestinal electrical or mechanical activity, but rather overrides the latter and imposes motility patterns that are entirely externally controlled by an implantable microprocessor;

(b) calls for implantation of electrode sets (either from the serosal or from the mucosal side) around the circumference of the organ, but the electrode axes themselves could be collinear or perpendicular to the organ axis (see for example FIGS. 1A-1D);

(c) utilizes external signals with extended frequency and amplitude range, and with extended timing parameters depending on the desired application (see for example FIGS. 2A-2C, FIGS. 5A-5C and FIG. 7);

(d) calls for synchronized sphincter control by exhausting the ACh patches in the vicinity of the organ with an appropriate timing (see for example FIGS. 9A, 9b, 10A, 10B, 11A and 11B);

(e) induces forward or reversed peristalsis, or asynchronous contractile desynchronization with appropriate and programmable intensity so that the patient would not experience discomfort, pain, nausea or vomiting;

(f) suggests innovative and versatile power supply options using transcutaneous inductive link for battery recharging or for complete power transfer in the framework of an implantable microsystem (see for example FIGS. 12, 13).

A number of inventions have been disclosed in this patent disclosure and it will be appreciated that not all features disclosed here form part of all of the inventions. The embodiments disclosed are exemplary of the inventions.

What is claimed is:

1. A method of control of a gastrointestinal tract, or a portion thereof, the gastrointestinal tract, or portion thereof, comprising a pylorus, the method comprising the steps of:
    electrically stimulating patches in the vicinity of the pylorus until the pylorus relaxes; and
    applying electrical energy to the gastrointestinal tract or a portion thereof to invoke a desired motility response of the gastrointestinal tract.

2. The method of claim 1 in which the desired response is delayed emptying of the stomach.

3. The method of claim 1 in which the desired response is peristalsis.

4. The method of claim 3 in which applying electrical energy to the gastrointestinal tract comprises electrically overriding the spontaneous mechanical activity of the gastrointestinal tract or a portion thereof.

5. The method of claim 4 in which applying electrical energy to the gastrointestinal tract is caffied out asynchronously with the spontaneously existing mechanical activity of the gastrointestinal tract.

6. The method of claim 5 in which electrically oveffiding the spontaneous mechanical activity of the gastrointestinal tract or a portion thereof is caffied out using electrical signals that are varied in voltage.

7. The method of claim 6 in which electrically oveffiding the spontaneous mechanical activity of the gastrointestinal tract or a portion thereof is caffied out using electrical energy having a duty cycle less than 100%.

8. The method of claim 1 in which the desired response is externally-controlled peristalsis.

9. The method of claim 1 in which the desired response is externally-controlled delayed movement of contents through the gastrointestinal tract.

10. The method of claim 1 in which the electrical energy has a variable voltage and a duty cycle of less than 100%.

11. The method of claim 10 in which applying electrical energy to the gastrointestinal tract comprises electrically oveffiding the spontaneously existing mechanical activity in the gastrointestinal tract or in a portion thereof, in which the oveffiding is carried out asynchronously with spontaneously existing motility of the gastrointestinal tract.

12. The method of claim 11 in which:
    the electrodes are implanted in a series of pairs along the gastrointestinal tract; and
    the electrical pattern overriding the spontaneously existing motility of the gastrointestinal tract comprises sequential, overlapping or embedded excitation signals applied to the pairs of electrodes.

13. The method of claim 11 in which energy for the electrical oveffiding pattern is transmitted wireles sly and transcutaneously to an implanted receiver.

14. The method of claim 10 in which the duty cycle is between 10% and 90%.

15. The method of claim 10 in which the duty cycle is between 50% and 90%.

16. The method of claim 10 in which energy is transmitted to the electrodes by wirelessly transmitting energy transcutaneously to the electrodes.

17. The method of claim 10 in which the electrodes includes at least two sets of spaced apart electrodes, and the electrodes are energized to produce contractile desynchronization of muscles of the gastrointestinal tract.

18. The method of claim 17 in which the electrodes are energized randomly.

19. Apparatus for control of gastrointestinal motility, the apparatus compnsing:
    an implant incorporating gastrointestinal tract electrodes; and
    a controller for delivering energy to the gastrointestinal tract electrodes, the controller being configured to deliver a first electrical pattern to the electrodes to cause a muscle of the gastrointestinal tract to relax after a prolonged controlled contraction, and a second electrical pattern to the electrodes to cause a desired response of the gastrointestinal tract.

20. The apparatus of claim 19 in which the controller is configured to deliver the second electrical pattern as a pattern that oveffides the spontaneously existing mechanical activity of the gastrointestinal tract.

* * * * *

UNITED STATES PATENT AND TRADEMARK OFFICE
CERTIFICATE OF CORRECTION

PATENT NO. : 7,343,201 B2
APPLICATION NO. : 11/000325
DATED : March 11, 2008
INVENTOR(S) : M. P. Mintchev It is certified that error appears in the above-identified patent and that said Letters Patent is hereby corrected as shown below:

| COLUMN | LINE | ERROR |
|---|---|---|
| 9 (Claim 5, | 25 line 2) | "caffied" should read --carried-- |
| 9 (Claim 6, | 28 line 1) | "oveffiding" should read --overriding-- |
| 9 (Claim 6, | 30 line 2) | "caffied" should read --carried-- |
| 9 (Claim 7, | 32 line 1) | "oveffiding" should read --overriding-- |
| 9 (Claim 7, | 34 line 3) | "caffied" should read --carried-- |
| 10 (Claim 11, | 1 line 3) | "oveffiding" should read --overriding-- |
| 10 (Claim 11, | 3 line 5) | "oveffiding" should read --overriding-- |
| 10 (Claim 13, | 13 line 2) | "oveffiding" should read --overriding-- |
| 10 (Claim 13, | 13 line 2) | "wireles sly" should read --wirelessly-- |

UNITED STATES PATENT AND TRADEMARK OFFICE
CERTIFICATE OF CORRECTION

PATENT NO. : 7,343,201 B2
APPLICATION NO. : 11/000325
DATED : March 11, 2008
INVENTOR(S) : M. P. Mintchev It is certified that error appears in the above-identified patent and that said Letters Patent is hereby corrected as shown below:

| COLUMN | LINE | ERROR |
|---|---|---|
| 10 (Claim 19, | 29 line 2) | "compnsing:" should read --comprising:-- |
| 10 (Claim 20, | 41 line 3) | "oveffides" should read --overrides-- |

Signed and Sealed this

Thirtieth Day of December, 2008

JON W. DUDAS
*Director of the United States Patent and Trademark Office*